(12) United States Patent
Evans

(10) Patent No.: US 7,527,605 B2
(45) Date of Patent: May 5, 2009

(54) MEDICAL-BALLOON INFLATOR

(75) Inventor: Stephen W. Evans, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 584 days.

(21) Appl. No.: 11/168,674

(22) Filed: Jun. 28, 2005

(65) Prior Publication Data
US 2007/0010788 A1 Jan. 11, 2007

(51) Int. Cl.
*A61M 29/00* (2006.01)
(52) U.S. Cl. .................. 604/97.02; 604/97.01
(58) Field of Classification Search ............ 604/97.01, 604/97.02; 222/327
See application file for complete search history.

(56) References Cited
U.S. PATENT DOCUMENTS

| | | | | |
|---|---|---|---|---|
| 4,802,479 A | * | 2/1989 | Haber et al. ............... | 606/192 |
| 4,808,165 A | * | 2/1989 | Carr ........................... | 604/97.02 |
| 4,940,459 A | * | 7/1990 | Noce .......................... | 604/97.02 |
| 5,209,731 A | * | 5/1993 | Sterman et al. ........... | 604/97.02 |
| 5,306,248 A | * | 4/1994 | Barrington ................ | 604/97.02 |
| 5,507,727 A | * | 4/1996 | Crainich ................... | 604/97.02 |
| 5,873,499 A | * | 2/1999 | Leschinsky et al. ...... | 222/327 |
| 5,893,488 A | * | 4/1999 | Hoag et al. ................ | 222/391 |
| 6,286,729 B1 | * | 9/2001 | Lin ............................ | 222/391 |

OTHER PUBLICATIONS

Sears Online Catalog http://www.sears.com/sr/javasr/catalog/product Craftsman Professional 7 in. Pliers, RoboGrip with Curved Jaw.

* cited by examiner

*Primary Examiner*—Nicholas D Lucchesi
*Assistant Examiner*—Victoria P Campbell
(74) *Attorney, Agent, or Firm*—Gerry S. Gressel

(57) ABSTRACT

A medical-balloon inflator includes a pump piston assembly, a movable pivot, and an actuator handle. The actuator handle is operatively connected to the movable pivot and is adapted to translate the pump piston assembly to inflate or inflatingly pressurize a medical balloon when the actuator handle is rotated an angular distance about the movable pivot by a user.

16 Claims, 3 Drawing Sheets

MEDICAL-BALLOON INFLATOR

FIELD OF THE INVENTION

The present invention is related generally to medical instruments, and more particularly to a medical-balloon inflator.

BACKGROUND OF THE INVENTION

Conventional medical-balloon inflators include those whose pump handle is repeatedly pumped a number of times (ten to twenty times in one example) to inflate a particular medical balloon to a desired inflation size, wherein it becomes harder for a user to pump the pump handle as the inflation pressure increases (up to a high pressure of between eight to twelve atmospheres in one example). Medical balloons include those used, in one common application, to dilate strictures in the esophagus of a patient. In one known example, an esophageal medical balloon is attached to the distal end of a catheter whose proximal end is attached to the pump outlet of the conventional medical-balloon inflator.

Conventional pliers and conventional tree-branch pruning shears include those having a movable pivot which provides variable leverage. One known example is Craftsman Robo-Grip® pliers sold by Sears.

Still, scientists and engineers continue to seek improved medical-balloon inflators.

SUMMARY

A first expression of an embodiment of the invention is for a medical-balloon inflator including a medical-balloon-inflator housing, a pump piston assembly, a movable pivot, and an actuator handle. The medical-balloon-inflator housing has a pump outlet operatively connectable to a medical balloon. The pump piston assembly is located in the housing and is operatively connected to the pump outlet. The actuator handle is operatively connected to the movable pivot and is adapted to translate the pump piston assembly to inflate the medical balloon when the medical balloon is operatively connected to the pump outlet and when the actuator handle is rotated an angular distance about the movable pivot by a user. The movable pivot has spaced-apart first and second pivot locations.

A second expression of an embodiment of the invention is for a medical-balloon inflator including a medical-balloon-inflator pump piston assembly and a ratcheting mechanism. The medical-balloon-inflator pump piston assembly is fluidly communicable with a medical balloon. The ratcheting mechanism includes a movable pivot and an actuator handle operatively connected to the movable pivot and adapted to translate the pump piston assembly to inflatingly pressurize the medical balloon when the medical balloon is in fluid communication with the pump piston assembly and when the actuator handle is rotated an angular distance about the movable pivot by a user. The movable pivot moves to increase mechanical advantage of the actuator handle with increasing pump-piston-assembly pressure.

A third expression of an embodiment of the invention is for a medical-balloon inflator including a medical-balloon-inflator housing, a pump piston assembly, a movable pivot, and an actuator handle. The medical-balloon-inflator housing has a pump-outlet luer fitting operatively connectable to a medical balloon. The pump piston assembly is located in the housing, is adapted to translatingly pressurize a liquid, and is operatively connected to the pump-outlet luer fitting. The actuator handle is operatively connected to the movable pivot and is adapted to translate the pump piston assembly to inflate the medical balloon when the medical balloon is operatively connected to the pump-outlet luer fitting and when the actuator handle is rotated an angular distance about the movable pivot by a user. The movable pivot moves from a first pivot location to a second pivot location to increase mechanical advantage of the actuator handle with increasing pump-piston-assembly pressure. The actuator handle includes first and second detents. The medical-balloon inflator also includes a fulcrum bar having a first end defining the movable pivot. The first end of the fulcrum bar is located in the first detent in the first pivot location, and the first end of the fulcrum bar is located in the second detent in the second pivot location.

Several benefits and advantages are obtained from one or more of the expressions of an embodiment of the invention. In one application, the movable pivot moves to a first pivot location providing the actuator handle with a small mechanical advantage but a large pressure increase. In this application, as balloon pressure (which is the same as piston-pump-assembly pressure) increased, the movable pivot moves to a second pivot location providing the actuator handle with a large mechanical advantage but a small pressure increase. In this application, the net effect is faster inflation of the medical balloon and improved control of balloon pressure due to the variable stroke action provided by the movable pivot.

DETAILED DESCRIPTION

Before explaining the embodiment of the present invention in detail, it should be noted that the embodiment is not limited in its application or use to the details of construction and arrangement of parts and steps illustrated in the accompanying drawings and description. The illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is further understood that any one or more of the following-described expressions of the embodiment, examples, etc. can be combined with any one or more of the other following-described expressions of the embodiment, examples, etc.

Figure 1:
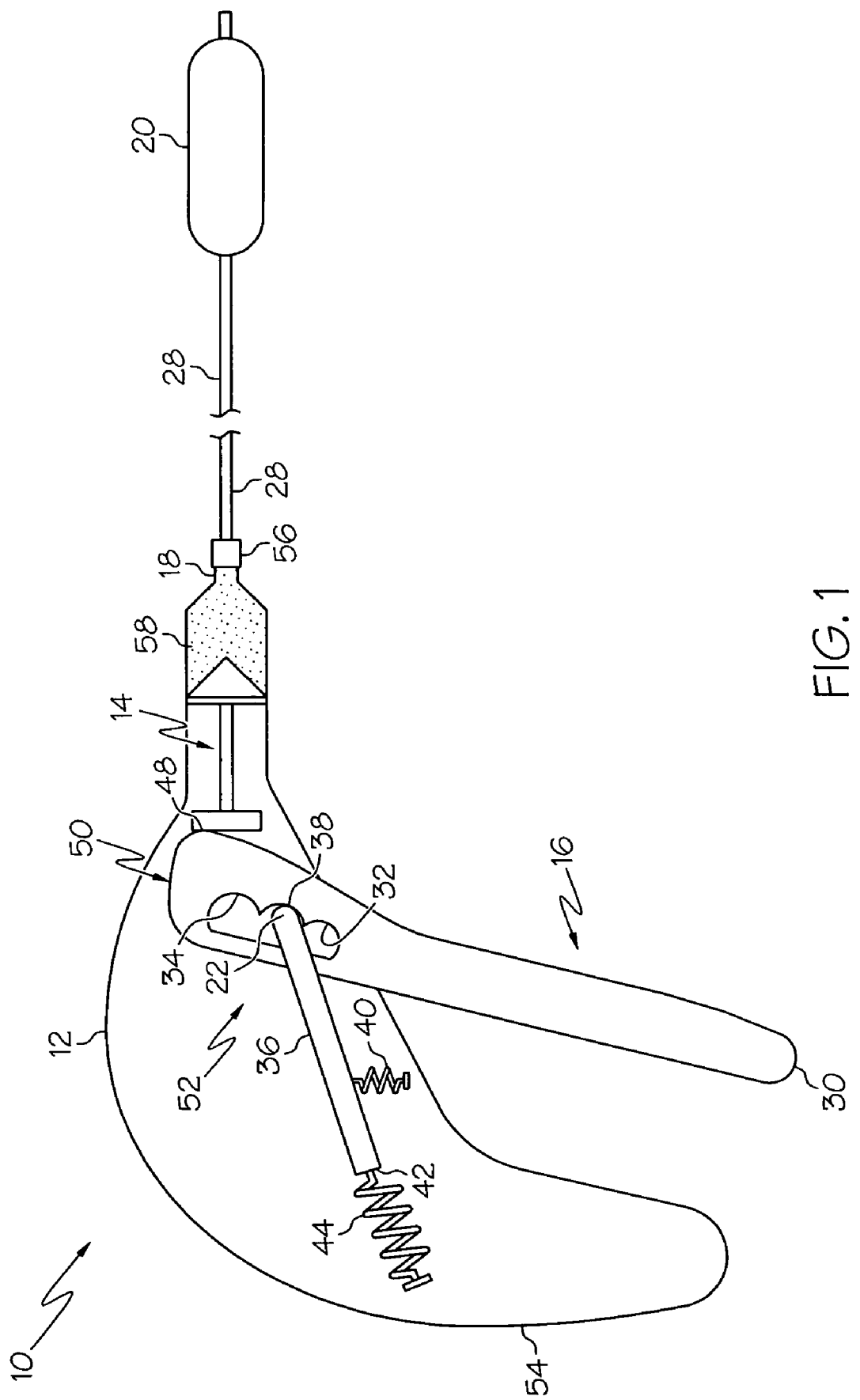
FIG. 1 is a schematic, side-elevational, cutaway view of an embodiment of a medical-balloon inflator of the invention shown connected to an end of a catheter whose other end is connected to a medical balloon.
Figure 2:
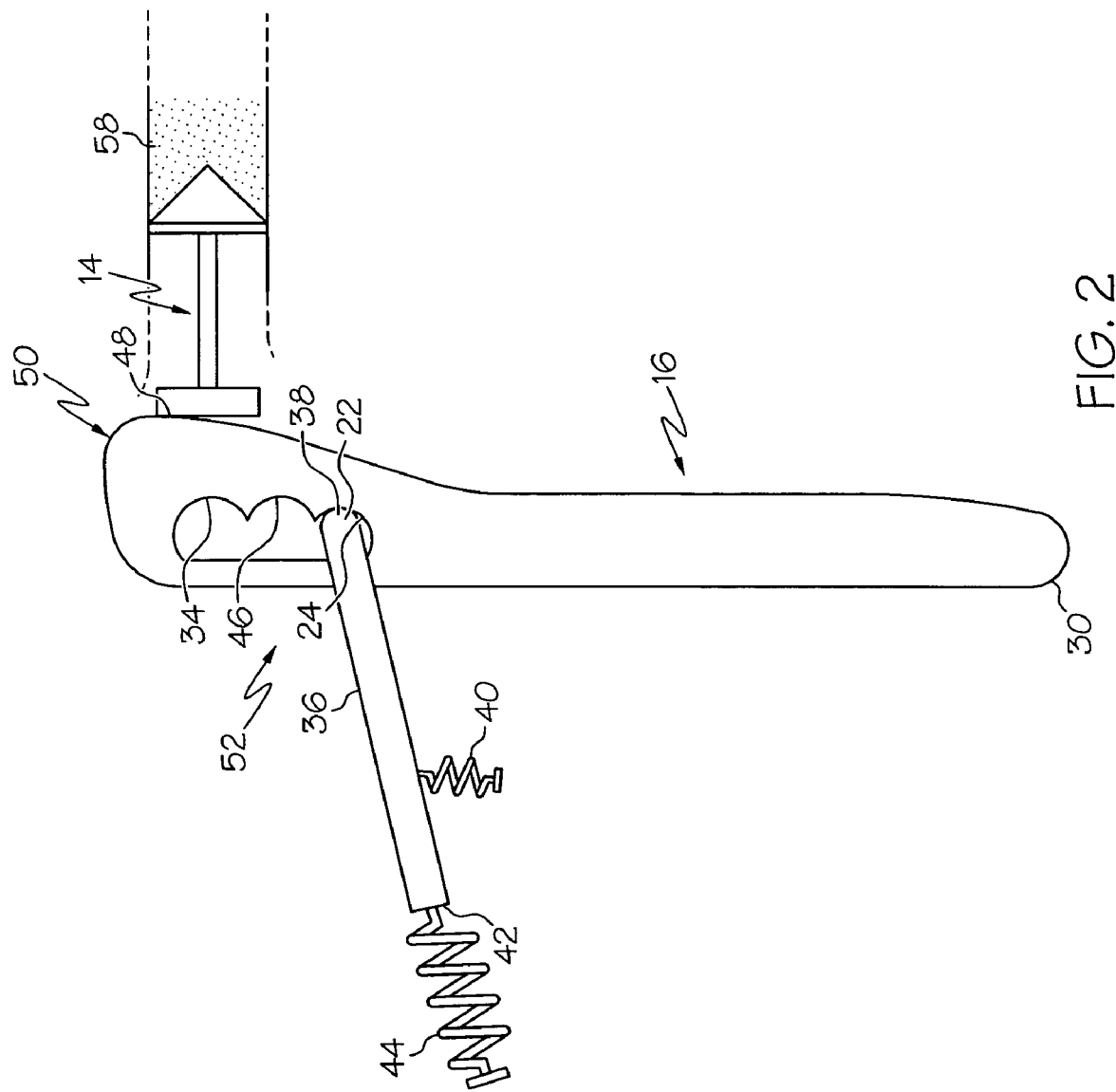
FIG. 2 is a view of the ratcheting mechanism and pump piston assembly of the medical-balloon inflator of FIG. 1 with the movable pivot located in a first pivot location.
Figure 3:
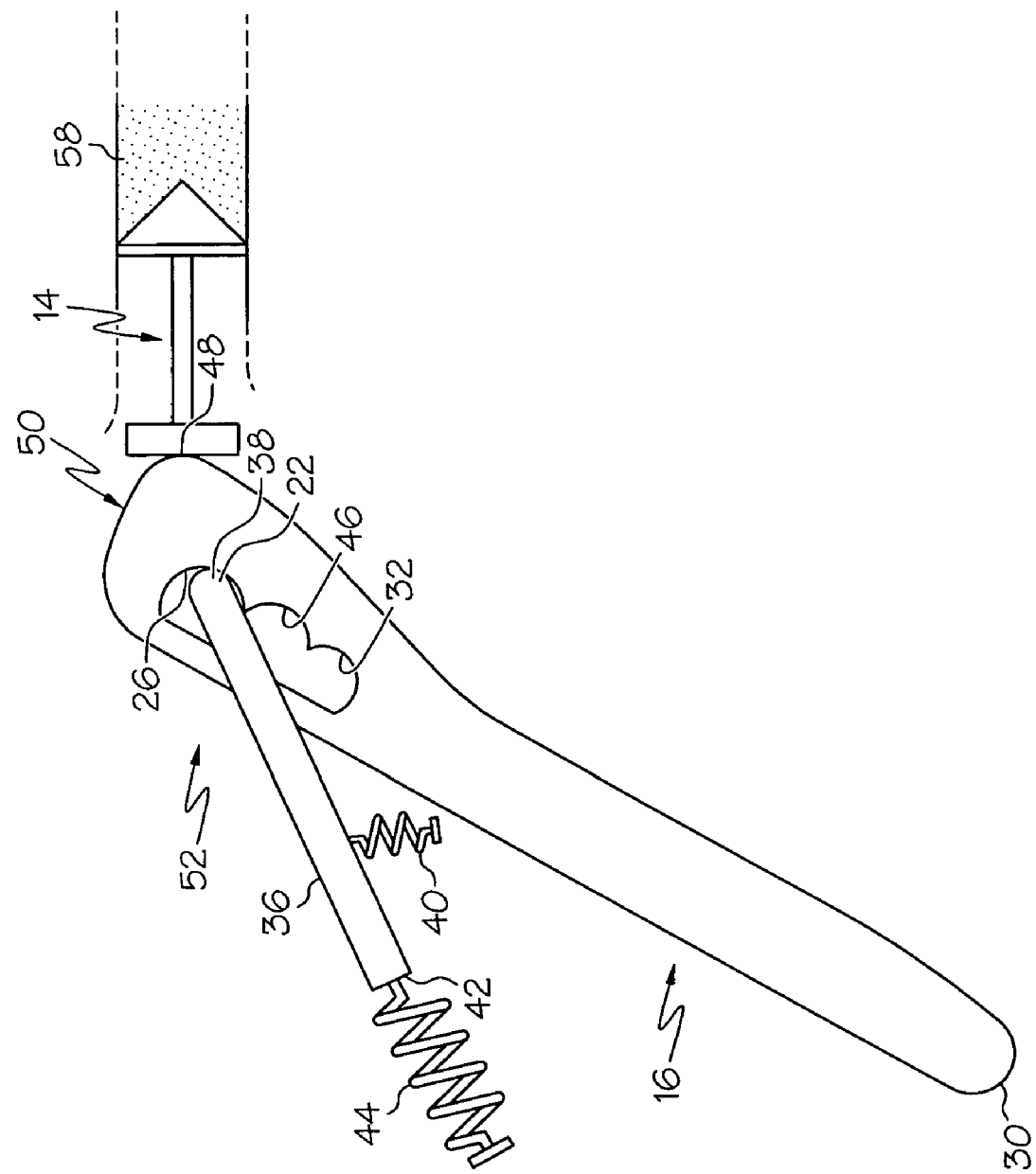
FIG. 3 is a view of the ratcheting mechanism and pump piston assembly of the medical-balloon inflator of FIG. 1 with the movable pivot located in a second pivot location.

An embodiment of a medical-balloon inflator 10 of the invention is shown in FIGS. 1-3. A first expression of the embodiment of FIGS. 1-3 is for a medical-balloon inflator 10 including a medical-balloon-inflator housing 12, a pump piston assembly 14, a movable pivot 22, and an actuator handle 16. The medical-balloon-inflator housing 12 has a pump outlet 18 operatively connectable to a medical balloon 20. The pump piston assembly 14 is disposed in the housing 12 and is operatively connected to the pump outlet 18. The actuator handle 16 is operatively connected to the movable pivot 22 and is adapted to translate the pump piston assembly 14 to inflate the medical balloon 20 when the medical balloon 20 is operatively connected to the pump outlet 18 and when the actuator handle 16 is rotated an angular distance about the movable pivot 22 by a user. The movable pivot 22 has spaced-apart first and second pivot locations 24 and 26.

In one implementation of the first expression of the embodiment of FIGS. 1-3, the pump outlet 18 is operatively connectable to a medical balloon 20 through an intervening catheter 28, wherein, when operatively connected, the pump outlet 18 is fluidly connected to the proximal end of the catheter 28 and the medical balloon 20 is fluidly connected to the distal end of the catheter 28. In one application, the distal end of the catheter, with a fluidly connected but uninflated medical balloon, is inserted into the esophagus of a patient, and, when the medical balloon is in position, a user rotates the actuator handle 16 to inflate the medical balloon 20 to dilate an esophageal stricture. Other implementations and applications are left to the artisan.

In one construction of the first expression of the embodiment of FIGS. 1-3, the actuator handle 16 has a free end 30, and the distance from the free end 30 to the first pivot location 24 is shorter than the distance from the free end 30 to the second pivot location 26. In one variation, the movable pivot 22 is at the first pivot location 24 (as seen in FIG. 2) before the actuator handle 16 is rotated by the user, and the movable pivot 22 is at the second pivot location 26 (as seen in FIG. 3) when the actuator handle 16 is rotated the angular distance about the movable pivot 22 by the user.

In one arrangement of the first expression of the embodiment of FIGS. 1-3, the actuator handle 16 includes first and second detents 32 and 34, and the medical-balloon inflator 10 also includes a fulcrum bar 36 having a first end 38 defining the movable pivot 22. In one variation, the first end 38 of the fulcrum bar 36 is disposed in the first detent 32 in the first pivot location 24, and the first end 38 of the fulcrum bar 36 is disposed in the second detent 34 in the second pivot location 26.

In one extension of the first expression of the embodiment of FIGS. 1-3, the medical-balloon inflator 10 also includes a return spring 40 operatively connected to the fulcrum bar 36 to return the first end 38 of the fulcrum bar 36 to engage the first detent 32 when the user releases the actuator handle 16. In one variation, the fulcrum bar 36 has a second end 42, and the medical-balloon inflator 10 also includes a resistance spring 44 operatively connected to the second end 42 of the fulcrum bar 36. In one modification, the actuator handle 16 includes a third detent 46 disposed between the first and second detents 32 and 34. In one example, the return spring 40 is fixedly attached to the housing 12, and the resistance spring 44 is attached to the movable portion of a ball joint (not shown) whose non-movable portion is fixedly attached to the housing 12. In one utilization, the housing 12 is a handpiece 54, and the user, using one or both hands, squeezes together, in one squeeze, the actuator handle 16 and the handpiece 54 to inflate the medical balloon 20. It is noted that by "squeezes together" is meant that the parts are squeezed toward each other whether they touch or not touch at the completion of the squeeze.

In one configuration of the first expression of the embodiment of FIGS. 1-3, the contact area 48 of the actuator handle 16 with the pump piston assembly 14 moves along the surface 50 of the actuator handle 16 as the actuator handle 16 is rotated by the user and the movable pivot 22 moves from the first detent 32 to the third detent 46 to the second detent 34, progressively by overcoming friction between the fulcrum bar 36 and the detents 32, 46, and 34, as can be appreciated by the artisan. That friction is determined largely by the stiffness of the resistance spring 44 and the height of the detents 32, 46 and 34. In one variation, the surface 50 of the actuator handle 16 is adapted to provide a smaller translation of the pump piston assembly 14 for the same change in rotation angle when the movable pivot 22 is in the second detent 34 than when the movable pivot 22 is in the first detent 32. In one modification, the resistance spring 44 is removed, and the return spring 40 is sized to perform the function of the resistance spring 44 as can be appreciated by those skilled in the art.

A second expression of the embodiment of FIGS. 1-3 is for a medical-balloon inflator 10 including a medical-balloon-inflator pump piston assembly 14 and a ratcheting mechanism 52. The medical-balloon-inflator pump piston assembly 14 is fluidly communicable with a medical balloon 20. The ratcheting mechanism 52 includes a movable pivot 22 and an actuator handle 16 operatively connected to the movable pivot 22 and adapted to translate the pump piston assembly 14 to inflatingly pressurize the medical balloon 20 when the medical balloon 20 is in fluid communication with the pump piston assembly 14 and when the actuator handle 16 is rotated an angular distance about the movable pivot 22 by a user. The movable pivot 22 moves to increase mechanical advantage of the actuator handle 16 with increasing pump-piston-assembly pressure.

In one employment of the second expression of the embodiment of FIGS. 1-3, the movable pivot 22 has spaced-apart first and second pivot locations 24 and 26, It is noted that the implementations, constructions, arrangements, etc. of the first expression of the embodiment of FIGS. 1-3 are equally applicable to the second expression of the embodiment of FIGS. 1-3.

A third expression of the embodiment of FIGS. 1-3 is for a medical-balloon inflator 10 including a medical-balloon-inflator housing 12, a pump piston assembly 14, a movable pivot 22, and an actuator handle 16. The medical-balloon-inflator housing 12 has a pump-outlet luer fitting 56 operatively connectable to a medical balloon 20. The pump piston assembly 14 is disposed in the housing 12, is adapted to translatingly pressurize a liquid 58, and is operatively connected to the pump-outlet luer fitting 56. The actuator handle 16 is operatively connected to the movable pivot 22 and is adapted to translate the pump piston assembly 14 to inflate the medical balloon 20 when the medical balloon 20 is operatively connected to the pump-outlet luer fitting 56 and when the actuator handle 16 is rotated an angular distance about the movable pivot 22 by a user. The movable pivot 22 moves from a first pivot location 24 to a second pivot location 26 to increase mechanical advantage of the actuator handle 16 with increasing pump-piston-assembly pressure. The actuator handle 16 includes first and second detents 32 and 34. The medical-balloon inflator 10 also includes a fulcrum bar 36 having a first end 38 defining the movable pivot 22. The first end 38 of the fulcrum bar 36 is disposed in the first detent 32 in the first pivot location 24, and the first end 38 of the fulcrum bar 36 is disposed in the second detent 34 in the second pivot location 26.

In one example of the third expression of the embodiment of FIGS. 1-3, the liquid 58 is water or a saline solution. It is noted that the implementations, constructions, arrangements, etc. of the first expression of the embodiment of FIGS. 1-3 are equally applicable to the third expression of the embodiment of FIGS. 1-3.

Several benefits and advantages are obtained from one or more of the expressions of an embodiment of the invention. In one application, the movable pivot moves to a first pivot location providing the actuator handle with a small mechanical advantage but a large pressure increase. In this application, as balloon pressure (which is the same as piston-pump-assembly pressure) increased, the movable pivot moves to a second pivot location providing the actuator handle with a large mechanical advantage but a small pressure increase. In this application, the net effect is faster inflation of the medical balloon and improved control of balloon pressure due to the variable stroke action provided by the movable pivot.

While the present invention has been illustrated by a description of several expressions of an embodiment and implementations, arrangements, etc. thereof, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended claims.

What is claimed is:

1. A medical-balloon inflator comprising:
   a) a medical-balloon-inflator housing having a pump outlet operatively connectable to a medical balloon;
   b) a pump piston assembly disposed in the housing and operatively connected to the pump outlet;
   c) a movable pivot;
   d) an actuator handle having first and second detents, and also including a fulcrum bar having a first end defining a movable pivot wherein the first end of the fulcrum bar is disposed in the first detent in the first pivot location, and wherein the first end of the fulcrum bar is disposed in the second detent in the second pivot location; the actuator handle being operatively connected to the movable pivot and adapted to translate the pump piston assembly to inflate the medical balloon when the medical balloon is operatively connected to the pump outlet and when the actuator handle is rotated an angular distance about the movable pivot by a user, wherein the movable pivot has spaced-apart first and second pivot locations wherein the actuator handle has a free end, and wherein the distance from the free end to the first pivot location is shorter than the distance from the free end to the second pivot location and wherein the movable pivot is at the first pivot location before the actuator handle is rotated by the user, and wherein the movable pivot is at the second pivot location when the actuator handle is rotated the angular distance about the movable pivot by the user; and
   e) a return spring operatively connected to the fulcrum bar to return the first end of the fulcrum bar to engage the first detent when the user releases the actuator handle.

2. The medical-balloon inflator of claim 1, wherein the fulcrum bar has a second end, and also including a resistance spring operatively connected to the second end of the fulcrum bar.

3. The medical-balloon inflator of claim 1, wherein the actuator handle includes a third detent disposed between the first and second detents.

4. A medical-balloon inflator comprising:
   a) a medical-balloon-inflator pump piston assembly fluidly communicable with a medical balloon; and
   b) a ratcheting mechanism including a movable pivot and an actuator handle operatively connected to the movable pivot and adapted to translate the pump piston assembly to inflatingly pressurize the medical balloon when the medical balloon is in fluid communication with the pump piston assembly and when the actuator handle is rotated an angular distance about the movable pivot by a user, wherein the movable pivot moves to increase mechanical advantage of the actuator handle with increasing pump-piston-assembly pressure.

5. The medical-balloon inflator of claim 4, wherein the movable pivot has spaced-apart first and second pivot locations, wherein the movable pivot is at the first pivot location before the actuator handle is rotated by the user, and wherein the movable pivot is at the second pivot location when the actuator handle is rotated the angular distance about the pivot by the user.

6. The medical-balloon inflator of claim 5, wherein the actuator handle includes first and second detents, and also including a fulcrum bar having a first end defining the movable pivot.

7. The medical-balloon inflator of claim 6, wherein the first end of the fulcrum bar is disposed in the first detent in the first pivot location, and wherein the first end of the fulcrum bar is disposed in the second detent in the second pivot location.

8. The medical-balloon inflator of claim 7, also including a return spring operatively connected to the fulcrum bar to return the first end of the fulcrum bar to engage the first detent when the user releases the actuator handle.

9. The medical-balloon inflator of claim 8, wherein the actuator handle has a free end, and wherein the distance from the free end to the first pivot location is shorter than the distance from the free end to the second pivot location.

10. The medical-balloon inflator of claim 8, wherein the fulcrum bar has a second end, and also including a resistance spring operatively connected to the second end of the fulcrum bar.

11. The medical-balloon inflator of claim 8, wherein the actuator handle includes a third detent disposed between the first and second detents.

12. A medical-balloon inflator comprising:
    a) a medical-balloon-inflator housing having a pump-outlet luer fitting operatively connectable to a medical balloon;
    b) a pump piston assembly disposed in the housing, adapted to translatingly pressurize a liquid, and operatively connected to the pump-outlet luer fitting;
    c) a movable pivot; and
    d) an actuator handle operatively connected to the movable pivot and adapted to translate the pump piston assembly to inflate the medical balloon when the medical balloon is operatively connected to the pump-outlet luer fitting and when the actuator handle is rotated an angular distance about the movable pivot by a user, wherein the movable pivot moves from a first pivot location to a second pivot location to increase mechanical advantage of the actuator handle with increasing pump-piston-assembly pressure, wherein the actuator handle includes first and second detents, and also including a fulcrum bar having a first end defining the movable pivot, wherein the first end of the fulcrum bar is disposed in the first detent in the first pivot location, and wherein the first end of the fulcrum bar is disposed in the second detent in the second pivot location.

13. The medical-balloon inflator of claim 12, also including a return spring operatively connected to the fulcrum bar to return the first end of the fulcrum bar to engage the first detent when the user releases the actuator handle.

14. The medical-balloon inflator of claim 13, wherein the fulcrum bar has a second end, and also including a resistance spring operatively connected to the second end of the fulcrum bar.

15. The medical-balloon inflator of claim 12, wherein the actuator handle includes a third detent disposed between the first and second detents.

16. A medical-balloon inflator comprising:
a) a medical-balloon-inflator housing having a pump outlet operatively connectable to a medical balloon;
b) a pump piston assembly disposed in the housing, having a proximal-most end and operatively connected to the pump outlet;
c) a movable pivot; and
d) an actuator handle operatively connected to the movable pivot, having a surface including a contact area in contact with the proximal-most end of the pump piston assembly, and adapted to translate the pump piston assembly to inflate the medical balloon when the medical balloon is operatively connected to the pump outlet and when the actuator handle is rotated an angular distance about the movable pivot by a user, wherein the movable pivot has spaced-apart first and second pivot locations, wherein the actuator handle has a free end, wherein the distance from the free end to the first pivot location is shorter than the distance from the free end to the second pivot location, wherein the movable pivot is at the first pivot location before the actuator handle is rotated by the user, and wherein, as the actuator handle is rotated the angular distance by the user, the contact area moves along the surface and the movable pivot moves from the first pivot location to the second pivot location.

* * * * *